United States Patent
Sancoff et al.

(10) Patent No.: US 6,679,895 B1
(45) Date of Patent: *Jan. 20, 2004

(54) APPARATUS AND METHOD FOR PLACING SUTURE WIRES INTO TISSUE FOR THE APPROXIMATION AND TENSIONING OF TISSUE

(75) Inventors: Gregory E. Sancoff, North Hampton, NH (US); Frederic P. Field, North Hampton, NH (US)

(73) Assignee: Onux Medical, Inc., Hampton, NH (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/706,472

(22) Filed: Nov. 3, 2000

Related U.S. Application Data (60) Provisional application No. 60/163,808, filed on Nov. 5, 1999.

(51) Int. Cl.$^7$ ................................................ A61B 17/04
(52) U.S. Cl. ...................................... 606/144; 606/148
(58) Field of Search ............................ 606/139, 144, 606/147, 148

(56) References Cited

U.S. PATENT DOCUMENTS

| | | | |
|---|---|---|---|
| 3,858,783 A | | 1/1975 | Kapitanov et al. |
| 4,103,690 A | | 8/1978 | Harris |
| 4,235,238 A | * | 11/1980 | Ogiu et al. ................. 606/148 |
| 4,306,560 A | | 12/1981 | Harris |
| 4,669,473 A | * | 6/1987 | Richards et al. ............ 606/148 |
| 5,499,990 A | * | 3/1996 | Schulken et al. ........... 606/103 |
| 5,507,754 A | * | 4/1996 | Green et al. ................ 606/148 |
| 6,332,889 B1 | * | 12/2001 | Sancoff et al. ............. 606/139 |
| 6,383,208 B1 | * | 5/2002 | Sancoff et al. ............. 606/144 |

* cited by examiner

*Primary Examiner*—Gary Jackson
(74) *Attorney, Agent, or Firm*—Pandiscio & Pandiscio (57) ABSTRACT

A suture placer for placing a length of suture wire through tissue such that the suture wire is directed into the tissue and then back out again.

17 Claims, 11 Drawing Sheets

APPARATUS AND METHOD FOR PLACING SUTURE WIRES INTO TISSUE FOR THE APPROXIMATION AND TENSIONING OF TISSUE

REFERENCE TO PENDING PRIOR PATENT APPLICATION

This patent application claims benefit of pending prior U.S. Provisional Patent Application Serial No. 60/163,808, filed Nov. 5, 1999 by Gregory E. Sancoff et al. for DEVICE FOR PLACING SUTURE WIRES INTO TISSUE FOR APPROXIMATION AND TENSION, which pending prior patent application is hereby incorporated herein by reference.

FIELD OF THE INVENTION

This invention relates to surgical apparatus and methods in general, and more particularly to apparatus and methods for placing suture wires into tissue for the surgical approximation and tensioning of tissue.

BACKGROUND OF THE INVENTION

There is a growing trend to perform many surgical procedures using minimally invasive techniques. In such surgery, which is sometimes referred to as "keyhole surgery", surgical instruments are inserted into the body through small surface incisions, and then the instruments are manipulated from outside the body while the actual surgery is carried out at a remote site inside the body.

One of the more common surgical tasks is the placement of sutures into tissue so as to aid repair. However, conventional suturing requires a substantial amount of manipulation, i.e., the needle must be moved safely into position at the surgical site, then the needle (and trailing suture) must be passed through the target tissue, then the needle must be safely removed from the surgical site, and finally the suture must be effectively knotted. During minimally invasive surgery, this must all be done at a remote interior surgical site, using a minimum of space. This can be difficult and time-consuming to do.

As a result, one object of the present invention is to provide apparatus for quickly and easily placing suture wires into tissue for the approximation and tensioning of tissue.

Another object of the present invention is to provide a method for quickly and easily placing suture wires into tissue for the approximation and tensioning of tissue.

SUMMARY OF THE INVENTION

These and other objects are addressed by the present invention, which comprises an apparatus and method for placing suture wire through tissue, e.g., during minimally invasive surgery or during open surgery where space may be limited. The apparatus is configured so as to deliver suture wire to the distal end of a shaft, whereupon the wire is deflected so as to change directions and pass into, and through, the tissue. As a result of this construction, the suture wire can be made to follow a path such that the wire goes into the tissue and then back out again, whereby a loop of suture wire may be passed through the tissue. This loop of suture wire may then be used to approximate and/or tension the tissue.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts and further wherein.

DETAILED DESCRIPTION OF THE PREFERRED EMBODIMENTS

Figure 1:
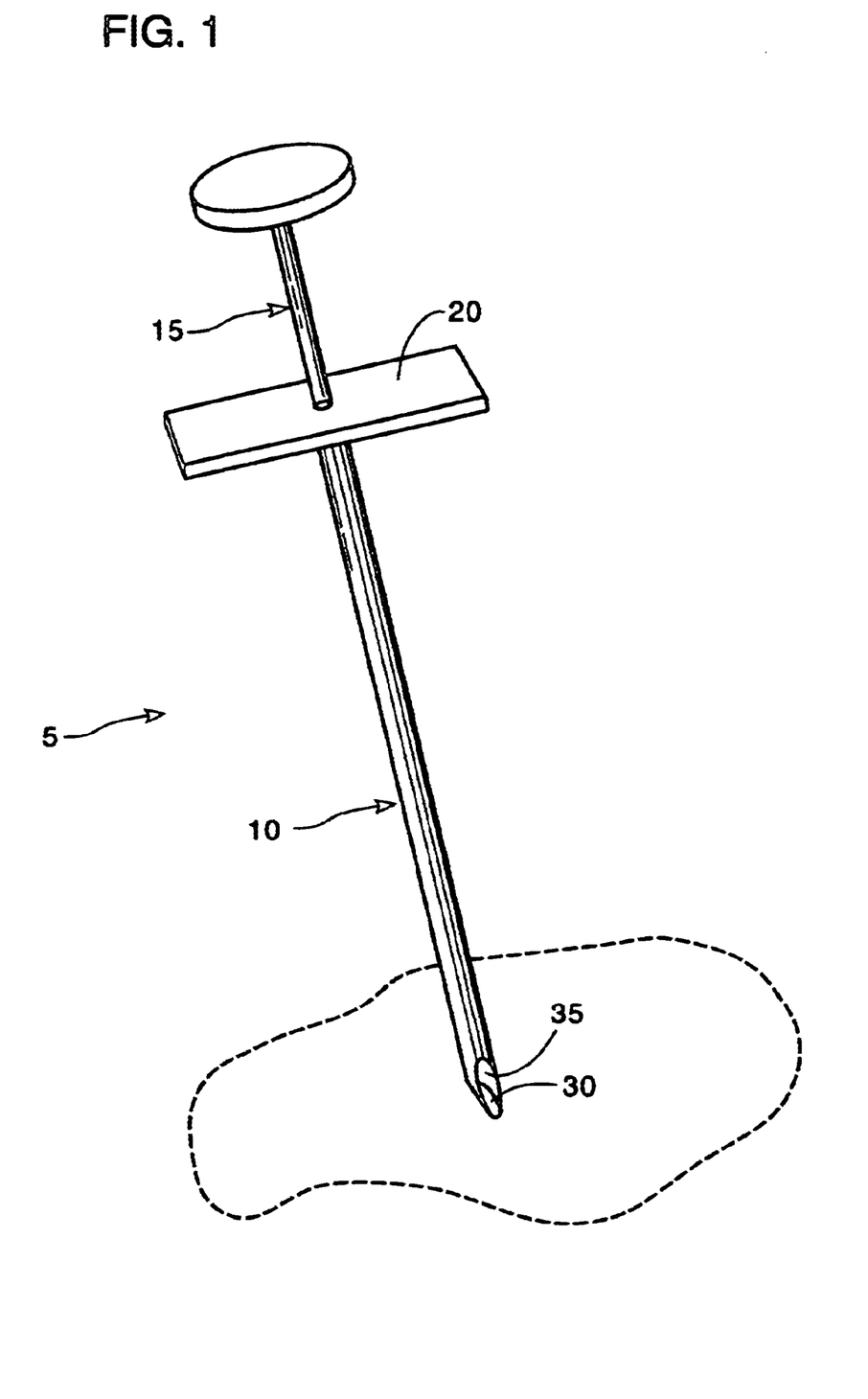
FIG. 1 is a perspective view of a suture placer formed in accordance with the present invention.
Figure 2:
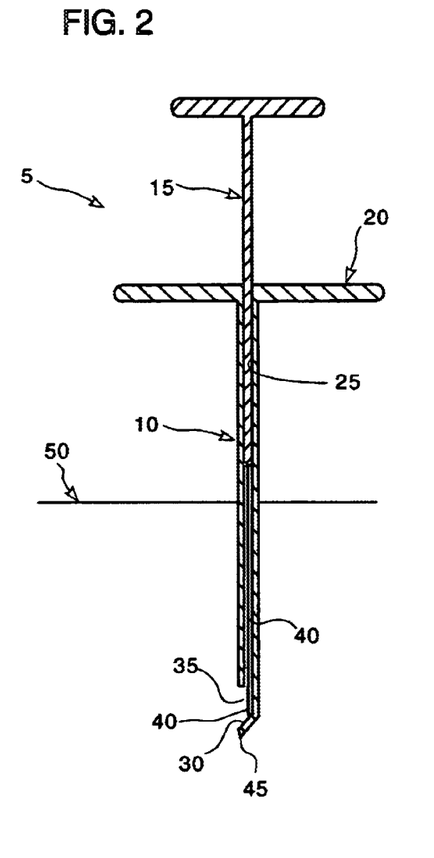
FIGS. 2 and 3 are sectional views showing operation of the suture placer of FIG. 1.
Figure 3:
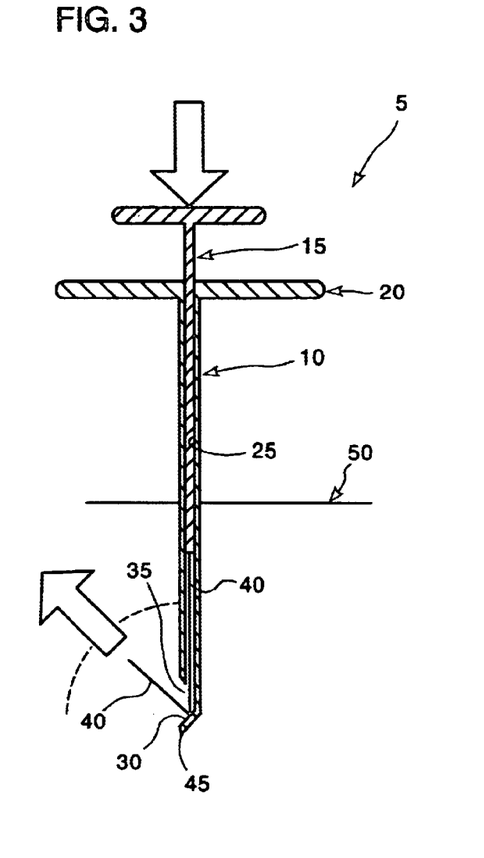

Looking first at FIGS. 1–3, there is shown a suture placer 5 formed in accordance with the present invention. Suture placer 5 generally comprises an elongated shaft 10 and a plunger 15. Shaft 10 has a crosshandle 20 at its proximal end, and contains a lumen 25 that runs from the proximal end of the shaft to a location near the distal end of the shaft.

At a location near the distal end of shaft 10, lumen 25 turns at a deflection die 30 and then proceeds out of the shaft through a side hole 35. Deflection die 30 is designed to turn a suture wire 40, passing distally down lumen 25, outward and backward (i.e., proximally). As a result, when the shaft's sharp distal tip 45 is placed in tissue 50, suture wire 40 travels below the surface of tissue 50 inside lumen 25 and, when the suture wire hits deflection die 30, the suture wire is deflected outward, through side hole 35, and backward up to the surface of tissue 50.

The shape of deflection die 30 helps determine the manner in which the suture wire changes direction at the distal end of the device.

More particularly, in one form of the invention, deflection die 30 is substantially planar (see FIGS. 1–3), whereby the deflection die will act as a simple deflection surface for redirecting the suture wire.

Figure 4:
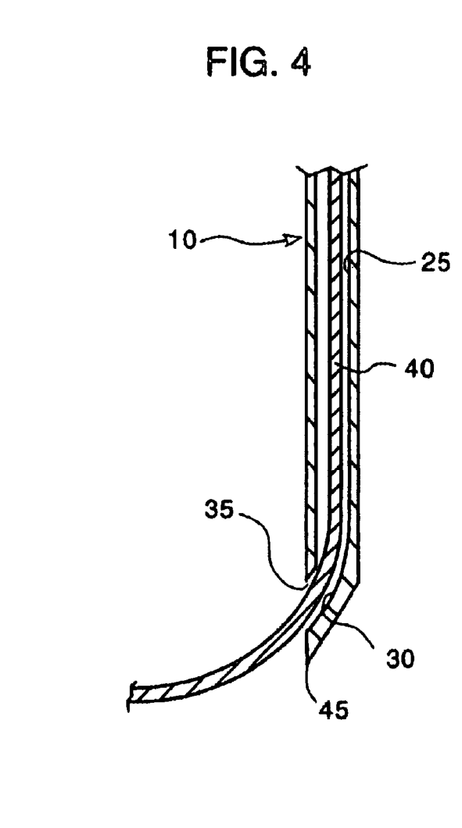
FIGS. 4 and 5 are enlarged sectional views showing several different deflection die shapes and the wire shapes that they create.
Figure 5:
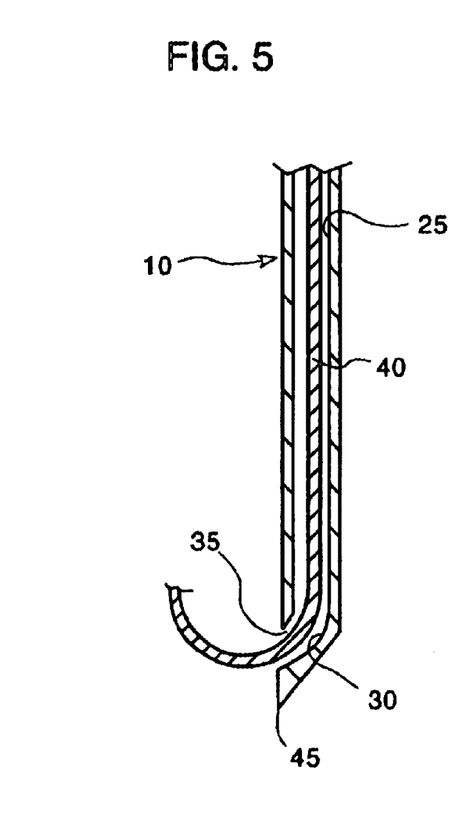

Alternatively, and more preferably, deflection die 30 is formed with a radius of curvature (see FIGS. 4 and 5), whereby the deflection die will cause suture wire 40 to take on a permanent set. In general, a sharper radius of curvature at the die surface causes a tighter wire loop (see FIGS. 4 and 5). The yield strength of the wire also helps determine the degree of wire curvature. In general, for a given deflection die and wire diameter, wire that has a higher yield strength will tend to permanently deform less, and therefore form a larger loop.

Figure 6:
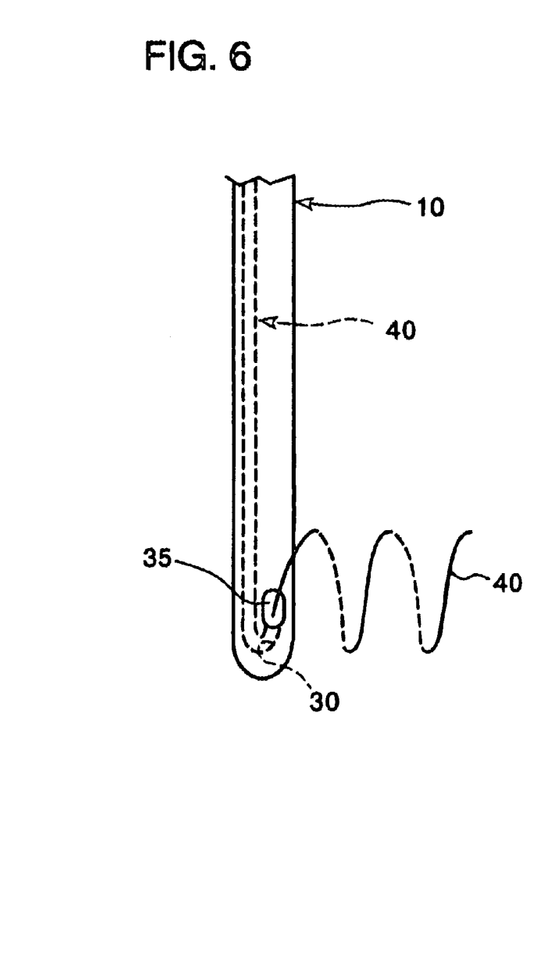
FIG. 6 is an enlarged schematic view showing another deflection die shape, wherein the deflection die shape also has a lateral curvature whereby to create a helical wire trajectory.

If deflection die 30 also includes a lateral radius, it will cause suture wire 40 to adopt a helical trajectory (see FIG. 6). A helical trajectory can be desirable where the distal end of suture wire 40 is to be burrowed into tissue 50, or where the suture wire is to be passed through a side wall of tissue 50, etc.

Suture wire 40 is contained within lumen 25 of shaft 10 and is laterally supported as the suture wire is advanced. To this end, the lumen diameter is preferably formed so as to be slightly larger than the diameter of the suture wire it is to receive (e.g., the lumen diameter might be 0.0055–0.0060 inches where the wire diameter is 0.0050 inches). This slight gap between suture wire 40 and lumen 25 is provided in order to avoid line-to-line contacts or, even worse, press fits between the suture wire and the lumen wall which might be encountered with likely manufacturing tolerances. Such tight fits would cause undue resistance to wire movement. At the same time, however, too large a gap could allow the suture wire to buckle, thus causing resistance to forward motion and also presenting a crumpled appearance along the length of the wire.

Figure 7:
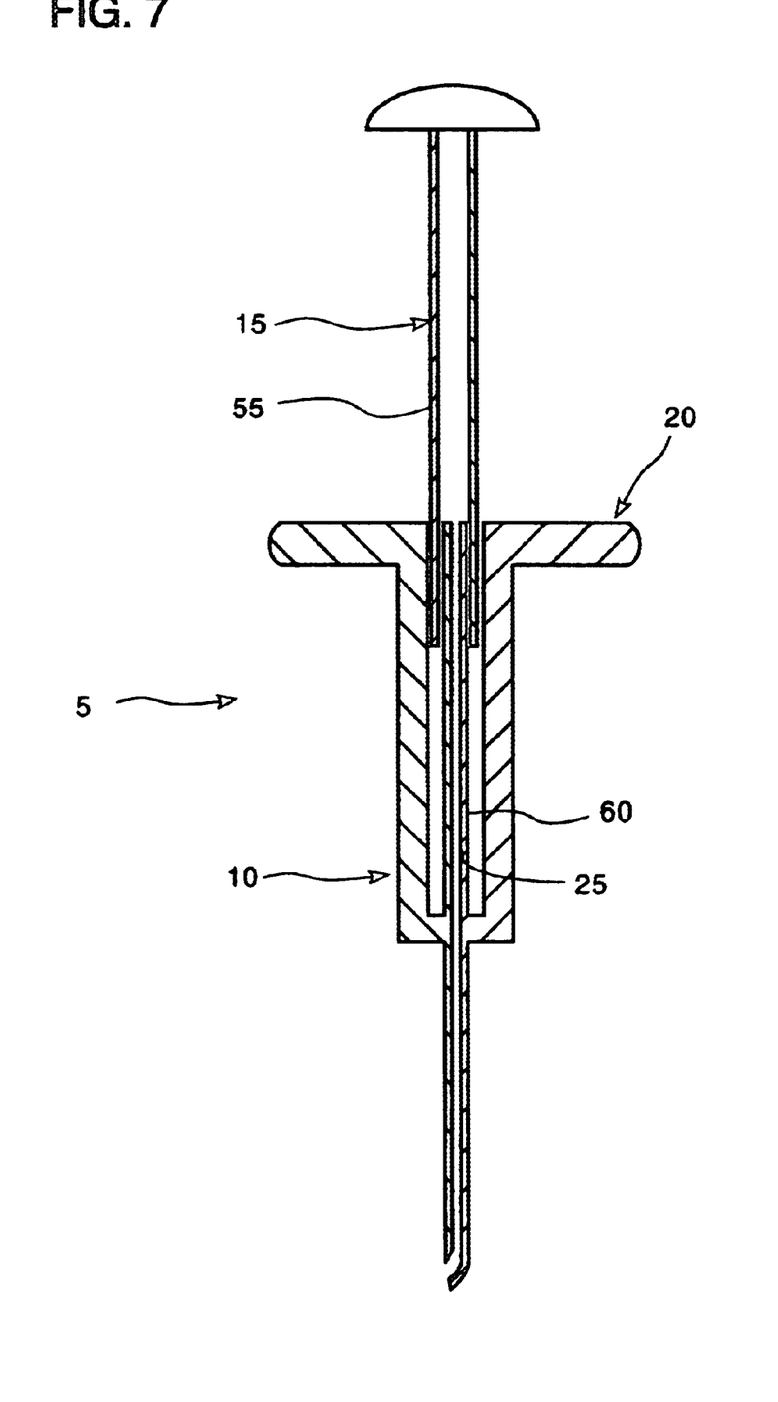
FIG. 7 is a sectional view of an alternative form of suture placer that uses telescopic tubing to advance the suture wire.

For smaller diameter wires, the plunger diameter may be too small to support the pushing load without the plunger buckling in the area outside of lumen 25 (i.e., in the area above crosshandle 20). Consequently, an alternative arrangement can be used that provides more support for the plunger. One such arrangement, shown in FIG. 7, is to make plunger 15 in the form of a tube 55 which telescopes over another smaller tube 60 which supports the suture wire in its lumen 25. As long as the smaller tube 60 has a relatively thin wall, suture wire 40 can be reasonably supported in the areas where tubes 55 and 60 are not overlapping (i.e., in the area above crosshandle 20). In this respect it should be appreciated that the sizes of tubes 55 and 60 have been exaggerated somewhat in FIG. 7 so as to make the details of construction more readily apparent.

It will be appreciated that the suture placer 5. shown in FIGS. 1–7 is configured to deploy a single length of wire suture 40, whereupon a new length of wire suture 40 must be loaded into lumen 25. While such a device is quite useful, there are many surgical settings in which it would be beneficial to have a device that could place a plurality of wire suture lengths before reloading. FIGS. 8–11 illustrate one such suture placer 5A.

Figure 8:
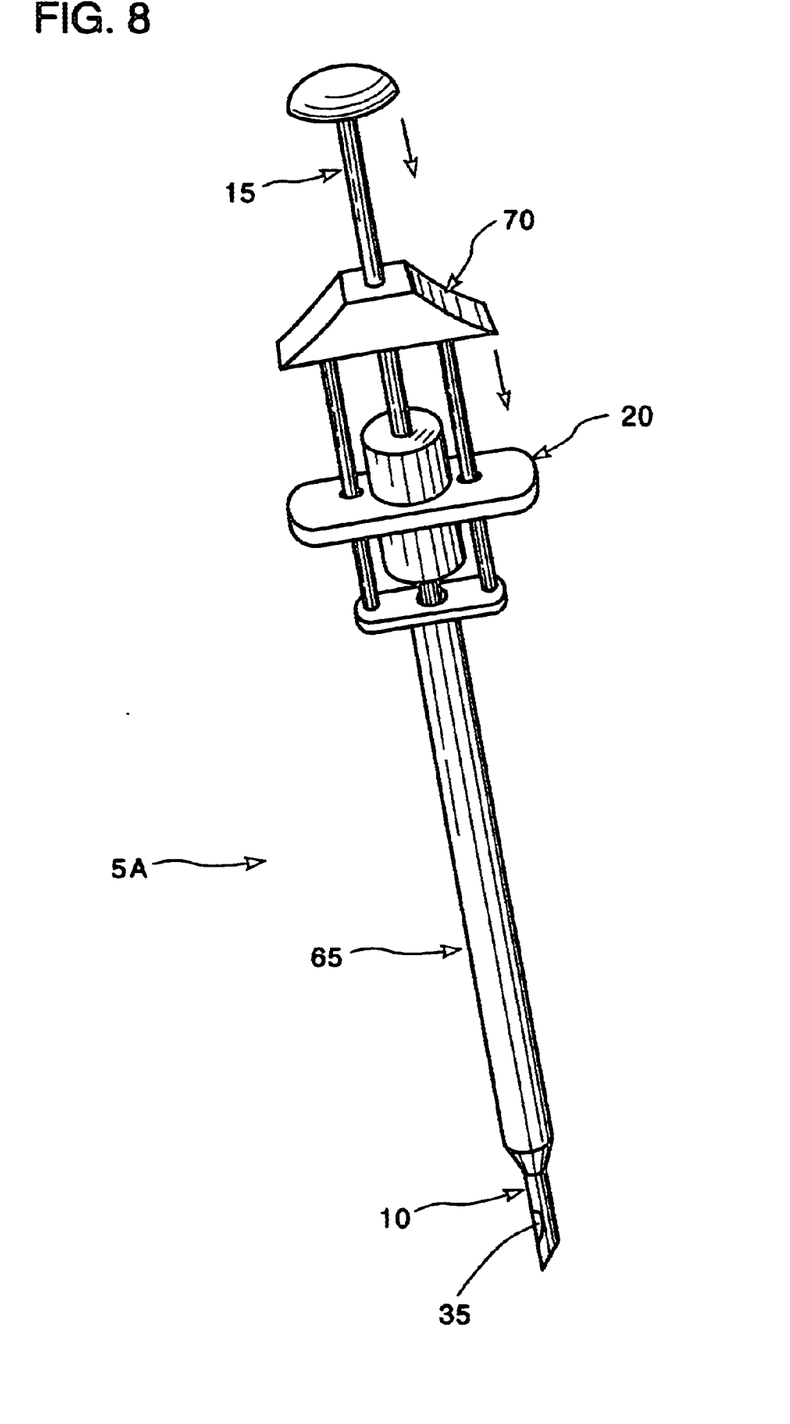
FIG. 8 is a perspective view of another alternative form of suture placer, wherein the suture placer is adapted to place multiple sutures in tissue, and includes wire cutting apparatus.

More particularly, suture placer 5A is substantially the same as the suture placer 5 described above, except that it has a cutting tube 65 on the outside of shaft 10. Cutting tube 65 is attached to a finger-operated tab 70 which, if moved forward (i.e., distally), slides cutting tube 65 downward so that the distal end of the cutting tube crosses the shaft's side hole 35 and shears off any suture wire 40 extending out of side hole 35, with a guillotine-type effect. If desired, the end of cutting tube 65 may be beveled so as to present a sharp edge to wire 40, whereby to make cutting easier.

Figure 9:
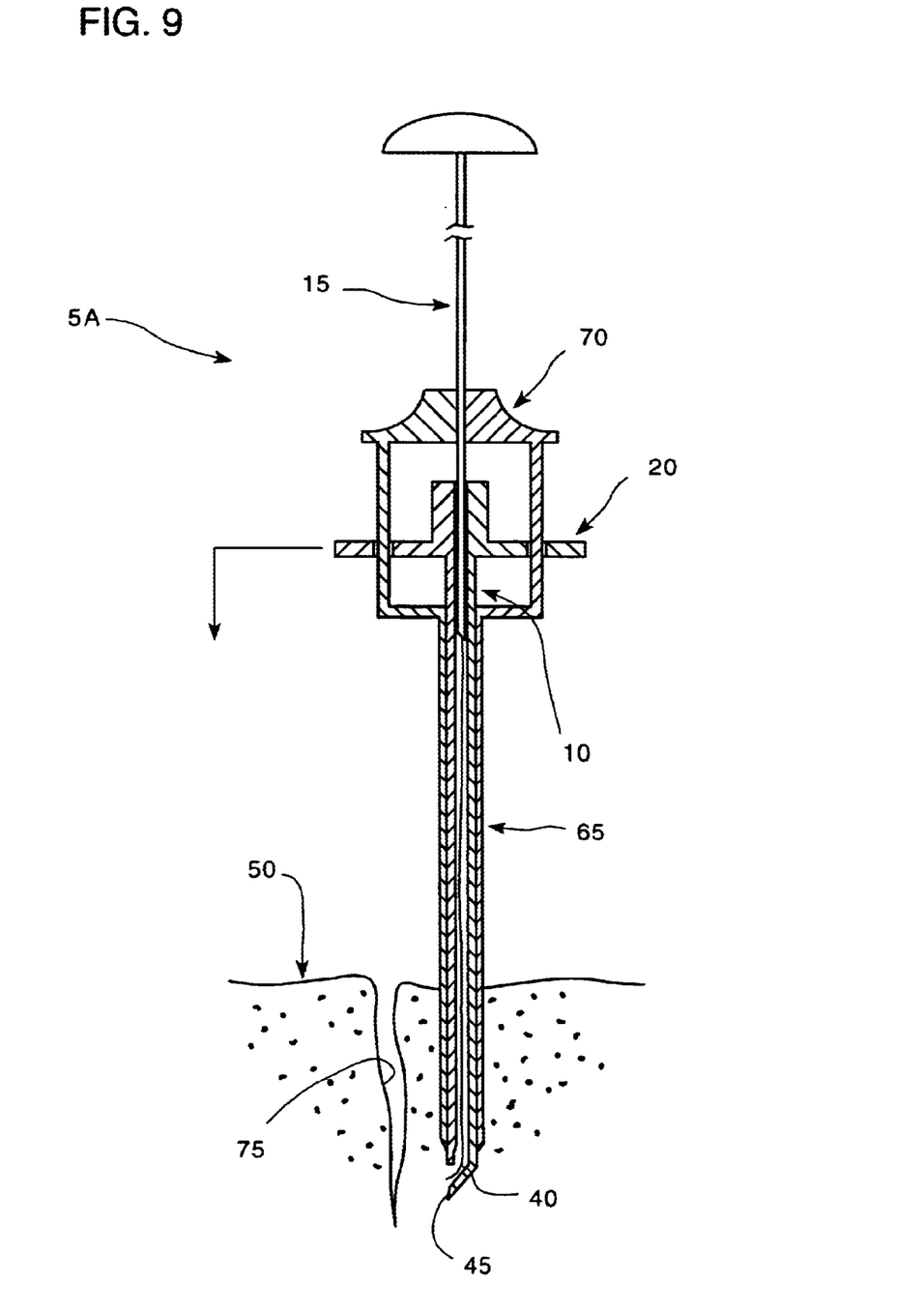
FIGS. 9, 10 and 11 are sectional views showing operation of the suture placer of FIG. 8.
Figure 10:
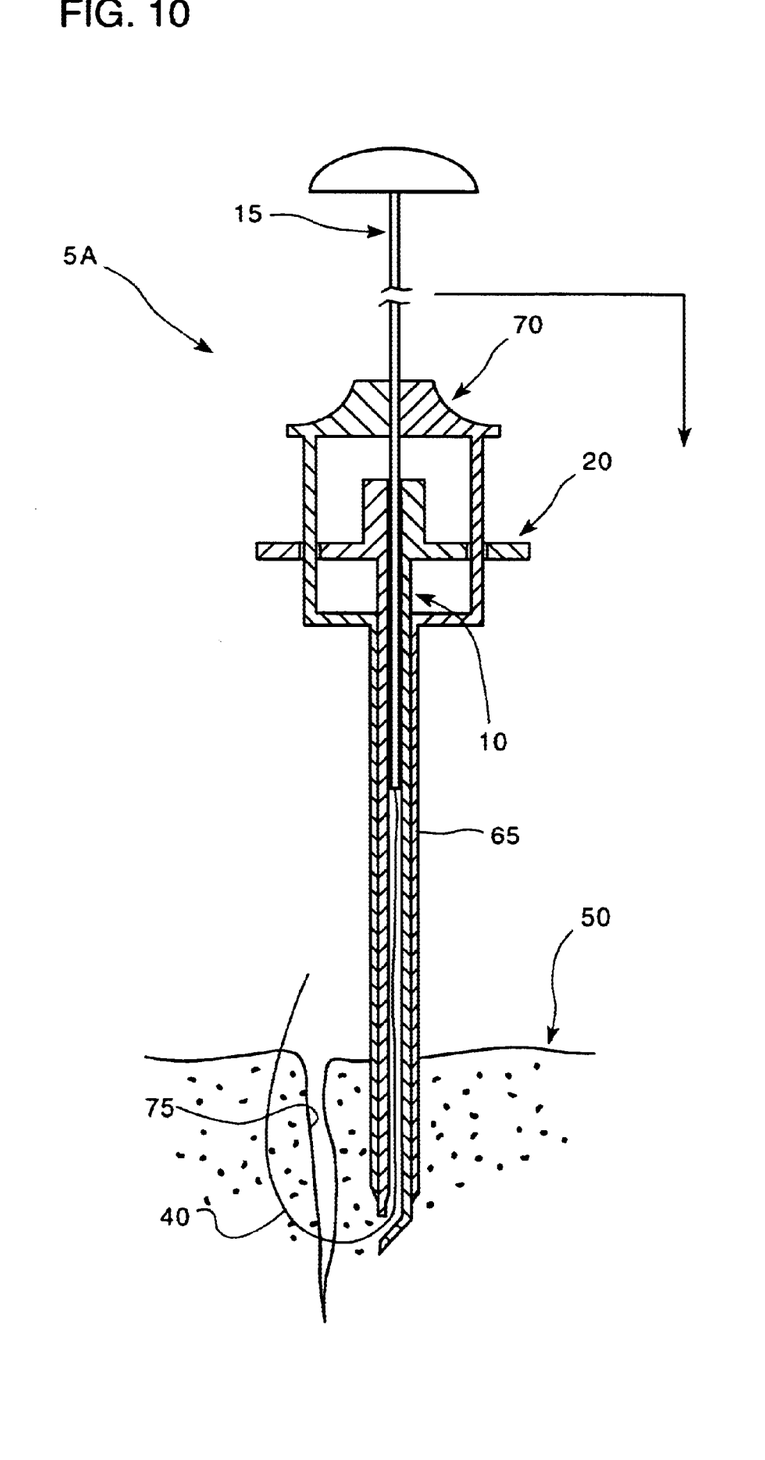
Figure 11:
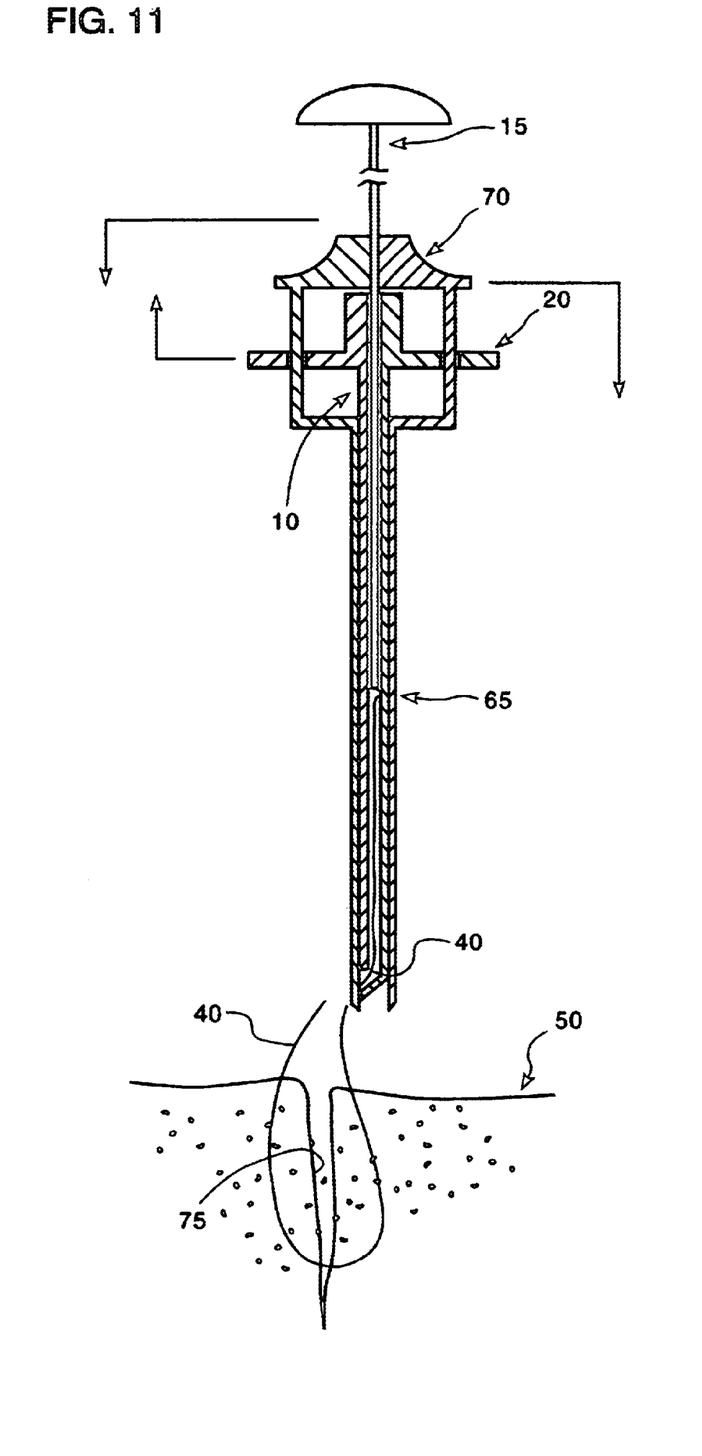
Figure 12:
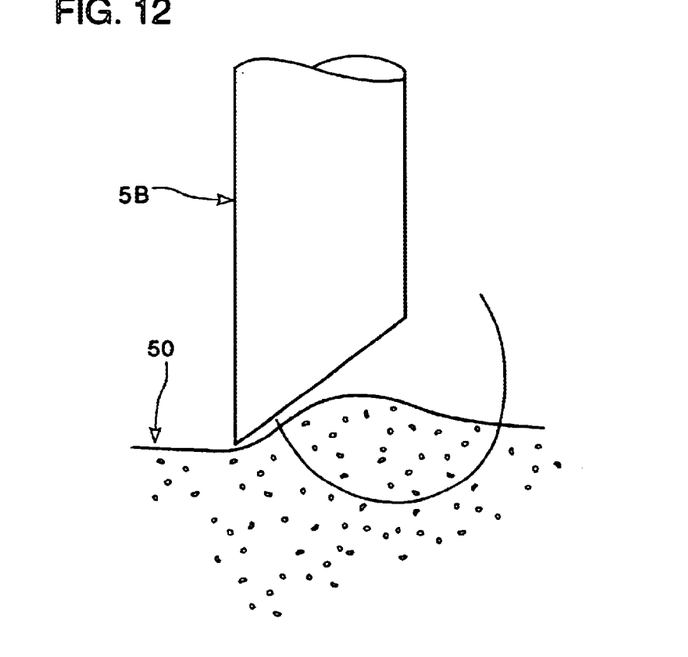
FIG. 12 is an enlarged side view of the distal end of still another alternative form of suture placer, wherein the suture placer is adapted to place suture into tissue from the surface of the tissue, without the suture placer penetrating the tissue with its shaft.
Figure 13:
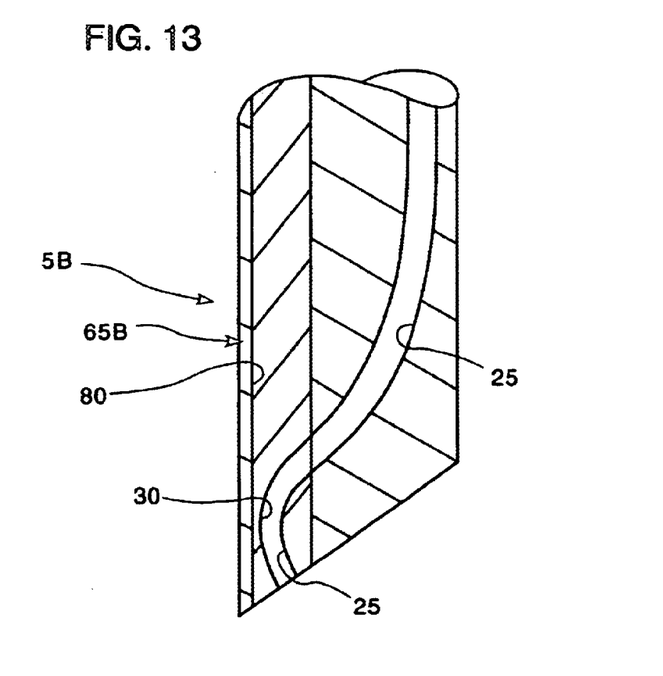
FIG. 13 is a sectional view of the suture placer shown in FIG. 12.
Figure 14:
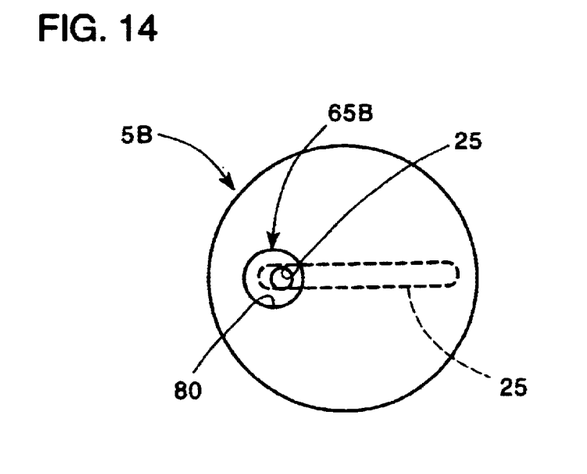
FIG. 14 is an end view of the suture placer shown in FIG. 12.

FIGS. 9–11 show how suture placer 5A may be used to place a length of wire suture 40 into tissue and then cut that length off from the remainder of the suture wire still in suture placer 5A. The first step is to place the sharp tip of shaft 10 into tissue 50 near where it is desired to put the suture, e.g., near a laceration 75 (FIG. 9). The next step is to advance suture wire 40 by pushing down on plunger 15 until the suture wire emerges from tissue 50 with sufficient length (FIG. 10). Then suture placer 5A is withdrawn from tissue 50 while simultaneously advancing suture wire 40 with plunger 15 so that the suture wire that is already in tissue 50 will be left in its current position as suture placer 5A is withdrawn. Finally, cutting tube tab 70 is pushed forward (i.e., distally) so as to cause cutting tube 65 to sever suture wire 40, whereby to disconnect the length of suture wire deployed in tissue 50 from the suture wire remaining in suture placer 5A. The two free ends of the deployed suture wire can now be twisted together so as to close laceration 75 and tension the approximation.

It should also be appreciated that if suture wire 40 is made of a relatively stiff material, or if suture wire 40 has a relatively large diameter, the suture wire can have enough rigidity to pass through tissue in a circular arc on its own, without first being taken down into the tissue with a penetrating shaft. Again, a deflection die will govern the radius of the wire trajectory and, in this case, the depth of penetration of the suture wire into the tissue before it returns out of the tissue.

Figure 15:
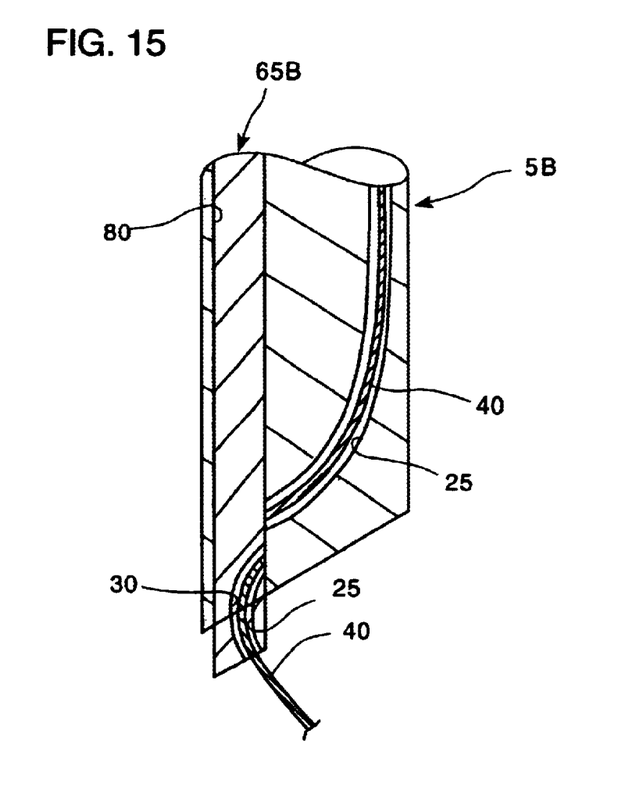
FIG. 15 is a sectional view like that of FIG. 13, but showing the suture placer with its cutting bar advanced distally.

More particularly, FIGS. 12–15 show the distal end of a suture passer 5B which is adapted to rest on the surface of tissue 50 as it passes a length of suture wire 40 therethrough. Suture passer 5B comprises a cutting bar 65B which is slidably received within a lumen 80 in shaft 10. Wire lumen 25 extends through shaft 10 and cutting bar 65B (see FIGS. 13–15). Cutting bar 65B also includes the deflection die 30 (see FIGS. 13 and 15). Inasmuch as the cutting bar 65B includes part of the wire lumen 25, when the cutting bar is displaced forward (i.e., distally) relative to shaft 10, the cutting bar will shear the suture wire against the lumen wall and cut it off (FIG. 15).

Figure 16:
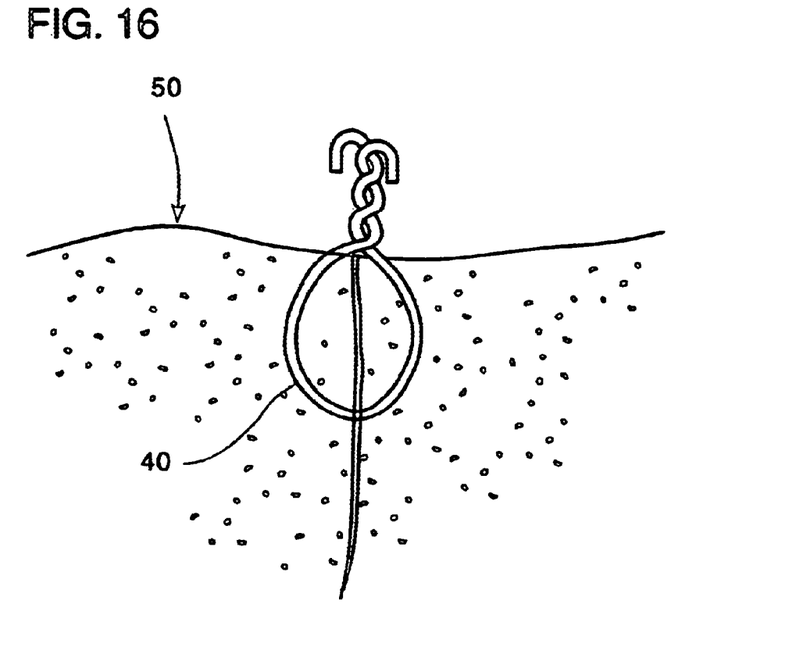
FIGS. 16 and 17 show two twisted knot embodiments.
Figure 17:
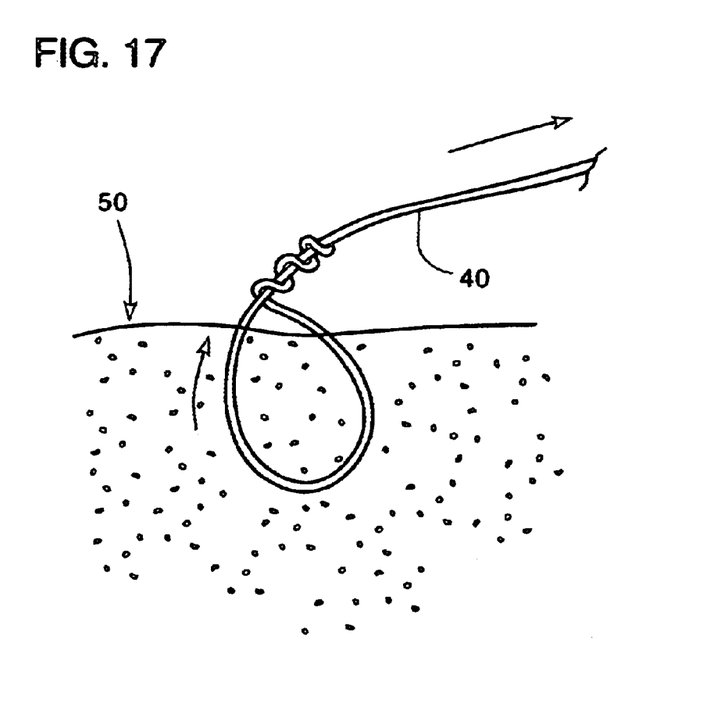

Once suture wire 40 has been placed through the tissue, the two free ends of the wire can be twisted together (FIG. 16), causing the closed loop of suture wire to become smaller, which in turn draws the tissue closer together. The excess can then be cut away and the proximal end of the twisted section bent downward, towards the tissue. Another option is to keep one end of the suture long after the twisted knot has been formed, so that the long suture end can be used to pull the tissue in some direction (see FIG. 17).

As used herein, the term "suture wire" is intended to mean any filament-like element consistent with the present invention. By way of example but not limitation, suture wire may comprise a metal (e.g., stainless steel, titanium, Nitinol or other shape memory alloy, etc.) or a plastic (e.g., polypropylene, polyimide, etc.), or other materials or combinations of materials.

It should be noted that the suture wire may have a configuration other than round, e.g., rectangular, square, elliptical, ribbon-like, etc. In this respect it should also be appreciated that a ribbon-like wire could provide increased lateral strength, resulting in more precise guidance as the suture wire passes through the tissue.

The present invention permits a wire suture to be placed into tissue at a remote surgical site, whereby that wire suture can be used for approximation and tensioning. Wire suture has the added benefit of acting as its own needle, so that holes larger than the suture itself need not be created.

What is claimed is:

1. Suture placer apparatus for placing a length of suture wire through tissue whereby the length of suture wire may thereafter be used to approximate and tension the tissue, said suture placer apparatus comprising:

a shaft having a proximal end and a distal end, a lumen extending through said shaft and sized to closely receive the suture wire for supported passage therethrough, said lumen exiting said shaft at a hole at said distal end of said shaft, and said distal end of said shaft being adapted to pierce the tissue so that said hole may be positioned below a surface of the tissue;

a deflection die located adjacent to said hole for engagement by a suture wire passing through said lumen, whereby the trajectory of the suture wire will be changed by said reflection die;

a cutting bar slidably disposed relative to said shaft, said cutting bar adapted to selectively intrude across said lumen so to selectively sever a piece of said suture wire extending within said lumen; and said suture wire being provided with an appropriate yield strength so as to allow permanent redirection of said suture wire away from said deflection die and so as to allow a distal end of said suture wire to penetrate tissue.

2. A suture placer apparatus according to claim 1 wherein said deflection die is substantially planar.

3. A suture placer apparatus according to claim 1 wherein said deflection die has a radius of curvature.

4. Suture placer apparatus according to claim 1 wherein said shaft is adapted to pierce tissue so that said hole may be positioned intermediate the tissue.

5. Suture placer apparatus according to claim 1 wherein said apparatus further comprises a length of suture wire disposed in said first lumen.

6. A method for approximating and tensioning tissue, comprising:

providing suture placer apparatus comprising:

a shaft having a proximal end and a distal end, a lumen extending through said shaft and sized to closely receive the suture wire for supported passage therethrough, said lumen exiting said shaft at a hole at said distal end of said shaft, and said distal end of said shaft being adapted to pierce the tissue so that said hole may be positioned below a surface of the tissue;

a deflection die located adjacent to said hole for engagement by a suture wire passing through said lumen, whereby the trajectory of the suture wire will be changed by said deflection die;

a cutting bar slidably disposed relative to said shaft, said cutting bar adapted to selectively intrude across said lumen so as to selectively sever a piece of said suture wire extending within said lumen; and said suture wire being provided with an appropriate yield strength so as to allow permanent redirection of said suture wire away from said deflection die and so as to allow a distal end of said suture wire to penetrate tissue;

positioning said distal end of shaft so that suture wire exiting said hole will penetrate said tissue; and advancing a length of suture wire through said lumen so that the suture wire engages said deflection die and is passed through said tissue.

7. Suture placer apparatus for placing a length of suture wire through tissue whereby the length of suture wire may thereafter be used to approximate and tension the tissue, said suture placer apparatus comprising:

a shaft having a proximal end and a distal end, and a lumen extending through said shaft and sized to closely receive the suture wire for supported passage therethrough, said lumen exiting said shaft at a hole at said distal end of said shaft;

a deflection die located adjacent to said hole for engagement by a suture wire passing through said lumen, whereby the trajectory of the suture wire will be changed by said deflection die;

a cutting bar slidably disposed relative to said shaft, said cutting bar adapted to selectively intrude across said lumen so as to selectively sever a piece of said suture wire extending within said lumen; and said suture wire being provided with an appropriate yield strength so as to allow permanent redirection of said suture wire away from said deflection die and so as to allow a distal end of said suture wire to penetrate tissue;

wherein said deflection die is substantially planar.

8. Suture placer apparatus for placing a length of suture wire through tissue whereby the length of suture wire may thereafter be used to approximate and tension the tissue, said suture placer apparatus comprising:

a shaft having a proximal end and a distal end, and a lumen extending through said shaft and sized to closely receive the suture wire for supported passage therethrough, said lumen exiting said shaft at a hole at said distal end of said shaft;

a deflection die located adjacent to said hole for engagement by a suture wire passing through said lumen, whereby the trajectory of the suture wire will be changed by said deflection die;

a cutting bar slidingly disposed relative to said shaft, said cutting bar adapted to selectively intrude across said lumen so as to selectively sever a piece of said suture wire extending within said lumen; and said suture wire being provided with an appropriate yield strength so as to allow permanent redirection of said suture wire away from said deflection die and so as to allow a distal end of said suture wire to penetrate tissue;

wherein said shaft is adapted to pierce tissue so that said hole may be positioned intermediate the tissue.

9. A suture placer according to claim 1 wherein said deflection die is configured within said cutting bar.

10. Suture placer apparatus for placing a length of suture wire through tissue whereby the suture wire may thereafter be used to approximate and tension the tissue, said suture placer apparatus comprising:

a shaft having a proximal end and a distal end, a lumen extending through said shaft and sized to closely receive the suture wire for supported passage therethrough, said lumen exiting said shaft at a hole at said distal end of said shaft, and said distal end of said shaft being adapted to pierce the tissue so that said hole may be positioned below a surface of the tissue;

a deflection die located adjacent to said hole for engagement by a suture wire passing through said lumen, whereby the trajectory of the suture wire will be changed by said deflection die;

a cutting tube disposed on an outside surface of said shaft, said cutting tube being positionable from a first position to a second position, said first position being located between said hole and said proximal end, said second position being located between said hole and said distal end, wherein said cutting tube is positionable from said first position to said second position so as to pass said hole and shear off the suture wire extending therefrom; and said suture wire being provided with an appropriate yield strength so as to allow permanent redirection of said suture wire away from said deflection die and so as to allow a distal end of said suture wire to penetrate tissue.

11. A suture placer apparatus according to claim 10 wherein said deflection die is substantially planar.

12. A suture placer apparatus according to claim 10 wherein said deflection die has a radius of curvature.

13. Suture placer apparatus according to claim 10 wherein said shaft is adapted to pierce tissue so that said hole may be positioned intermediate the tissue.

14. Suture placer apparatus according to claim 10 wherein said apparatus further comprises a length of suture wire disposed in said lumen.

15. A method for approximating and tensioning tissue, comprising:

providing suture placer apparatus comprising:

a shaft having a proximal end and a distal end, a lumen extending through said shaft and sized to closely receive the suture wire for supported passage therethrough, said lumen exiting said shaft at a hole at said distal end of said shaft, and said distal end of said shaft being adapted to pierce the tissue so that said hole may be positioned below a surface of the tissue;

a deflection die located adjacent to said hole for engagement by a suture wire passing through said lumen, whereby the trajectory of the suture wire will be changed by said deflection die;

a cutting tube disposed on an outside surface of said shaft, said kiting tube being positionable from a first position to a second position, said first position being located between said hole and said proximal end, said second position being located between said hole and said distal end, wherein said cutting tube is positionable from said first position to said second position so as to pass said hole and shear off the suture wire extending therefrom; and said suture wire being provided with an appropriate yield strength so as to allow permanent redirection of said suture wire away from said deflection die and so as to allow a distal end of said suture wire to penetrate tissue;

positioning said distal end of shaft so that suture wire exiting said hole will penetrate said tissue; and advancing a length of suture wire through said lumen so that the suture ire engages said deflection die and is passed through said tissue.

16. Suture placer apparatus for placing a length suture wire through tissue whereby the length of suture wire may thereafter be used to approximate and tension the tissue, said suture placer apparatus comprising:

a shaft having a proximal end and a distal end, and a lumen extending through said shaft and sized to closely receive the suture wire for supported passage therethrough, said lumen exiting said shaft at a hole at said distal end of said shaft;

a deflection die located adjacent to said hole for engagement by a suture wire passing through said lumen, whereby the trajectory of the suture wire will be changed by said deflection die;

a cutting tube disposed on an outside surface of said shaft, said cutting tube being positionable from a first position to a second position, said first position being located between said hole and said proximal end, said second position being located between said hole and said distal end, wherein said cutting tube is positionable from said first position to said second position so as to pass said hole and shear off the suture wire extending therefrom; and said suture wire being provided with an appropriate yield strength so as to allow permanent redirection of said suture wire away from said deflection die and so as to allow a distal end of said suture wire to penetrate tissue;

wherein said deflection die is substantially planar.

17. Suture placer apparatus for placing a length of suture wire through tissue whereby the length of suture wire may thereafter be used to approximate and tension the tissue, said suture placer apparatus comprising:

a shaft having a proximal end and a distal end, and a lumen extending through said shaft and sized to closely receive the suture wire for supported passage therethrough, said lumen exiting said shaft at a hole at said distal end of said shaft;

a deflection die located adjacent to said hole for engagement by a suture wire passing through said lumen, whereby the trajectory of the suture wire will be changed by said deflection die;

a cutting tube disposed on an outside surface of said shaft, said cutting tube being positionable from a first position to a second position, said first position being located between said hole and said proximal end, said second position being located between said hole and said distal end, wherein said cutting tube is positionable from said first position to said second position so as to pass said hole and shear off the suture wire extending therefrom; and said suture wire being provided with an appropriate yield strength so as to allow permanent redirection of said suture wire away from said deflection die and so as to allow a distal end of said suture wire to penetrate tissue;

wherein said shaft is adapted to pierce tissue so that said hole may be positioned intermediate the tissue.

* * * * *